United States Patent [19]

Hammerman et al.

[11] Patent Number: 5,898,090
[45] Date of Patent: Apr. 27, 1999

[54] AROMATIC ISOMERIZATION USING A MODIFIED SILICOALUMINOPHOSPHATE

[75] Inventors: John Ivor Hammerman, Arlington Heights, Ill.; Edith Marie Flanigen, White Plains, N.Y.; Gregory J. Gajda, Mount Prospect, Ill.; Jennifer S. Holmgren, Bloomingdale, Ill.; David A. Lesch, Hoffman Estates, Ill.; Robert Lyle Patton, Rolling Meadows, Ill.; Thomas Matthew Reynolds, Mobile, Ala.; Cara Moy Roeseler, Winfield, Ill.

[73] Assignee: UOP LLC, Des Plaines, Ill.

[21] Appl. No.: 08/992,357

[22] Filed: Dec. 17, 1997

Related U.S. Application Data

[63] Continuation-in-part of application No. 08/427,362, Apr. 24, 1995, abandoned.

[51] Int. Cl.$^6$ .................... C07C 5/22; C07C 2/02
[52] U.S. Cl. .................... 885/477; 585/481; 585/666; 585/529

[58] Field of Search .................... 585/527, 548, 585/529, 531, 533, 666, 607, 671, 477, 481

[56] References Cited

U.S. PATENT DOCUMENTS

| | | | |
|---|---|---|---|
| 4,440,871 | 4/1984 | Lok et al. | 502/214 |
| 4,740,650 | 4/1988 | Pellet et al. | 585/480 |
| 4,793,984 | 12/1988 | Lok et al. | 423/306 |
| 4,943,424 | 7/1990 | Miller | 423/328 |
| 5,087,347 | 2/1992 | Miller | 502/214 |
| 5,158,665 | 10/1992 | Miller | 423/205 |
| 5,208,005 | 5/1993 | Miller | 423/702 |
| 5,552,182 | 9/1996 | Evans | 423/701 |

*Primary Examiner*—Gary P. Straub
*Attorney, Agent, or Firm*—Thomas K. McBride; John F. Spears, Jr.; Richard E. Conser

[57] ABSTRACT

This invention is drawn to a process for isomerizing a non-equilibrium mixture of xylenes and ethylbenzene using a silicoaluminophosphate molecular sieve which is enriched in framework silicon at the surface, resulting in a greater yield of para-xylene compared to prior-art processes.

5 Claims, No Drawings

AROMATIC ISOMERIZATION USING A MODIFIED SILICOALUMINOPHOSPHATE

CROSS REFERENCE TO RELATED APPLICATION

This application is a continuation-in-part of application Ser. No. 08/427,362, filed Apr. 24, 1995, now abandoned, the contents of which are incorporated herein by reference.

FIELD OF THE INVENTION

This invention relates to catalytic hydrocarbon conversion, and more specifically to the use of an improved molecular-sieve catalyst in aromatics isomerization.

GENERAL BACKGROUND AND RELATED ART

Molecular sieves having a wide variety of compositions and structures have been disclosed in the art as useful in catalysts for hydrocarbon conversion. The most well known are the crystalline aluminosilicate zeolites formed from corner-sharing $AlO_2$ and $SiO_2$ tetrahedra. The zeolites generally feature pore openings of uniform dimensions, significant ion-exchange capacity and the capability of reversibly adsorbed an adsorbed phase which is dispersed throughout the internal voids of the crystal without displacing any atoms which make up the permanent crystal structure. Zeolites often are characterized by a critical, usually minimum, silica/alumina ratio.

More recently, a class of useful non-zeolitic molecular sieves containing framework tetrahedral units ($TO_2$) of aluminum ($AlO_2$), phosphorus ($PO_2$) and at least one additional element EL ($ELO_2$) has been disclosed. "Non-zeolitic molecular sieves" include the "ELAPSO" molecular sieves as disclosed in U.S. Pat. No. 4,793,984 (Lok et al.) and "SAPO" molecular sieves of U.S. Pat. No. 4,440,871 (Lok et al.). Generally the above patents teach a wide range of framework metal concentrations, e.g., the mole fraction of silicon in Lok et al. '871 may be between 0.01 and 0.98 depending on other framework elements with a preferable range of 0.02 to 0.25 mole fraction. U.S. Pat. No. 4,943,424 (Miller) discloses a silicoaluminophosphate molecular sieve characterized by surface and bulk $P_2O_5$-to-alumina ratios in the surface and bulk of the sieve and silicon content of the surface and its use in dewaxing and hydrocracking.

U.S. Pat. No. 4,740,650 (Pellet et al.) teaches xylene isomerization using a catalyst containing at least one non-zeolitic molecular sieve which preferably is a silicoaluminophosphate. Pellet et al do not suggest the critical composition gradients which are a feature of the present invention.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function. The former approach commonly results in higher ethylbenzene conversion, thus lowering the quantity of recycle to the para-xylene recovery unit and concomitant processing costs, but the latter approach enhances xylene yield by forming xylenes from ethylbenzene. A catalyst composite and process which enhance conversion according to the latter approach, i.e., achieve ethylbenzene isomerization to xylenes with high conversion, would effect significant improvements in xylene-production economics.

SUMMARY OF THE INVENTION

A principal object of the present invention is to provide a novel isomerization process for alkylaromatic hydrocarbons. More specifically, this invention is directed to isomerization of $C_8$-aromatic hydrocarbons using a critically defined molecular-sieve catalyst to obtain improved xylene yields.

This invention is based on the discovery that a catalyst comprising a SAPO molecular sieve having enriched surface silicon demonstrates improved conversion and selectivity in $C_8$-aromatics isomerization.

Accordingly, a broad embodiment of the invention is directed toward an alkylaromatics-isomerization process using a silicoaluminophosphate (SAPO) molecular-sieve catalyst having an enriched framework surface-silicon content. The process comprises isomerization preferably of a feedstock comprising a non-equilibrium mixture of xylenes and ethylbenzene at isomerization conditions to obtain a product having an increased para-xylene content relative to that of the feedstock. Preferably the SAPO-containing catalyst comprises a platinum-group metal, with platinum being an especially preferred component. The optimal catalyst composite also comprises an inorganic-oxide binder, usually alumina and/or silica.

These as well as other objects and embodiments will become evident from the following detailed description of the invention.

DETAILED DESCRIPTION OF THE INVENTION

As disclosed hereinabove, this invention is drawn to isomerization of alkylaromatics using a SAPO molecular-sieve catalyst having critical gradients of catalyst components.

The feedstock to aromatics isomerization comprises isomerizable alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include, for example but without so limiting the invention, ortho-xylene, meta-xylene, para-xylene, ethylbenzene, ethyltoluenes, tri-methylbenzenes, di-ethylbenzenes, tri-ethylbenzenes, methylpropylbenzenes, ethylpropylbenzenes, di-isopropylbenzenes, and mixtures thereof.

Isomerization of a $C_8$-aromatic mixture containing ethylbenzene and xylenes is a particularly preferred application of the SAPO sieves of the invention. Generally such mixture will have an ethylbenzene content in the approximate range of 5 to 50 mass-%, an ortho-xylene content in the approximate range of 0 to 35 mass-%, a meta-xylene content in the approximate range of 20 to 95 mass-% and a para-xylene content in the approximate range of 0 to 15 mass-%. It is preferred that the aforementioned $C_8$ aromatics comprise a non-equilibrium mixture, i.e., at least one $C_8$-aromatic isomer is present in a concentration that differs substantially (defined herein as a difference of at least 5 mass-% of the total $C_8$ aromatics) from the thermodynamic equilibrium concentration of that isomer at isomerization conditions. Usually the non-equilibrium mixture is prepared by removal of para- and/or ortho-xylene from a fresh $C_8$ aromatic mixture obtained from an aromatics-production process, and preferably the non-equilibrium mixture contains less than 5 mass-% para-xylene.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 mass-%. Preferably the isomerizable hydrocarbons consist essentially of aromatics, however, to ensure pure products from downstream recovery processes.

According to the process of the present invention, an alkylaromatic hydrocarbon feed mixture, preferably in admixture with hydrogen, is contacted with a catalyst of the type hereinafter described in an alkylaromatic hydrocarbon isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the feed mixture are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic feed mixture, preferably a non-equilibrium mixture of $C_8$ aromatics, is contacted with the isomerization catalyst at suitable alkylaromatic-isomerization conditions. Such conditions comprise a temperature ranging from about 0° to 600° C. or more, and preferably is in the range of from about 300° to 500° C. The pressure generally is from about 1 to 100 atmospheres absolute, preferably less than about 50 atmospheres. Sufficient catalyst is contained in the isomerization zone to provide a liquid hourly space velocity with respect to the hydrocarbon feed mixture of from about 0.1 to 30 h$^{-1}$, and preferably 0.5 to 10 hr$^{-1}$. The hydrocarbon feed mixture optimally is reacted in admixture with hydrogen at a hydrogen/hydrocarbon mole ratio of about 0.5:1 to about 25:1 or more. Other inert diluents such as nitrogen, argon and light hydrocarbons may be present.

The reaction proceeds via the mechanism, described hereinabove, of isomerizing xylenes while reacting ethylbenzene to form a xylene mixture via conversion to and reconversion from naphthenes. The yield of xylenes in the product thus is enhanced by forming xylenes from ethylbenzene. The loss of $C_8$ aromatics through the reaction thus is low: typically less than about 4 mass-% per pass of $C_8$ aromatics in the feed to the reactor, preferably about 3 mass-% or less, and most preferably no more than about 2.5 mass-%.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039,599, 4,184,943, 4,381,419 and 4,402,832, incorporated herein by reference thereto.

In a separation/isomerization process combination relating to the processing of an ethylbenzene/xylene mixture, a fresh $C_8$-aromatics feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, prior to para-xylene separation.

An essential component of the catalyst of the present invention is at least one non-zeolitic molecular sieve, also characterized as "NZMS" and defined in the instant invention to include molecular sieves containing framework tetrahedral units ($TO_2$) of aluminum ($AlO_2$), phosphorus ($PO_2$) and at least one additional element (EL) as a framework tetrahedral unit ($ELO_2$). "NZMS" includes the "SAPO" molecular sieves of U.S. Pat. No. 4,440,871, "ELAPSO" molecular sieves as disclosed in U.S. Pat. No. 4,793,984 and certain "MeAPO", "FAPO", "TAPO" and "MAPO" molecular sieves, as hereinafter described. Crystalline metal aluminophosphates (MeAPOs where "Me" is at least one of Mg, Mn, Co and Zn) are disclosed in U.S. Pat. No. 4,567,029, crystalline ferroaluminophosphates (FAPOs) are disclosed in U.S. Pat. No. 4,554,143, titanium aluminophosphates (TAPOs) are disclosed in U.S. Pat. No. 4,500,651, MAPO metal aluminophosphates wherein M is As, Be, B, Cr, Ga, Ge, Li or V are disclosed in U.S. Pat. No. 4,686,093, and binary metal aluminophosphates are described in Canadian Patent 1,241,943. ELAPSO molecular sieves also are disclosed in patents drawn to species thereof, including but not limited to GaAPSO as disclosed in U.S. Pat. No. 4,735,806, BeAPSO as disclosed in U.S. Pat. No. 4,737,353, CrAPSO as disclosed in U.S. Pat. No. 4,738,837, COAPSO as disclosed in U.S. Pat. No. 4,744,970, MgAPSO as disclosed in U.S. Pat. No. 4,758,419 and MnAPSO as disclosed in U.S. Pat. No. 4,793,833. The aforementioned patents are incorporated herein by reference thereto. The nomenclature employed herein to refer to the members of the aforementioned NZMSs is consistent with that employed in the aforementioned applications or patents. A particular member of a class is generally referred to as a "-n" species wherein "n" is an integer, e.g., SAPO-11, MeAPO-11 and ELAPSO-31. In the following discussion on NZMSs set forth hereinafter the mole fraction of the NZMS are defined as compositional values which are plotted in phase diagrams in each of the identified patents, published applications or copending applications.

The preferred non-zeolitic molecular sieves are the silicoaluminophosphate molecular sieves described in U.S. Pat. No. 4,440,871. The silicoaluminophosphate molecular sieves are disclosed as microporous crystalline silicoaluminophosphates, having a three-dimensional microporous framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from 0.02 to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, and represent the following values for "x", "y" and "z":

| | Mole Fraction | | |
|---|---|---|---|
| Point | x | y | z |
| A | 0.01 | 0.47 | 0.52 |
| B | 0.94 | 0.01 | 0.05 |
| C | 0.98 | 0.01 | 0.01 |
| D | 0.39 | 0.60 | 0.01 |
| E | 0.01 | 0.60 | 0.39 |

The silicoaluminophosphates of U.S. Pat. No. 4,440,871 are generally referred to therein as "SAPO" as a class, or as "SAPO-n" wherein "n" is an integer denoting a particular SAPO such as SAPO-11, SAPO-31, SAPO-40 and SAPO-41. The especially preferred species SAPO-11 as referred to herein is a silicoaluminophosphate having a characteristic X-ray powder diffraction pattern which contains at least the d-spacings set forth below:

| SAPO-11 | | |
|---|---|---|
| 2Θ | d | Relative Intensity |
| 9.4–9.65 | 9.41 – 9.17 | m |
| 20.3–20.6 | 4.37 – 4.31 | m |
| 21.0–21.3 | 4.23 – 4.17 | vs |
| 21.1–22.35 | 4.02 – 3.99 | m |
| 22.5–22.9 (doublet) | 3.95 – 3.92 | m |
| 23.15–23.35 | 3.84 – 3.81 | ms |

A preferred SAPO-11 for use in the present invention is SM-3 having a composition and properties in accordance with the teachings of U.S. Pat. No. 4,943,424 (Miller). SM-3 comprises a $P_2O_5$-to-alumina mole ratio at the surface of the silicoaluminophosphate of about 0.80 or less, preferably from about 0.80 to about 0.55; a $P_2O_5$-to-alumina mole ratio in the bulk of the SAPO of 0.96 or greater, preferably from about 0.96 to 1; and a silica-to-alumina mole ratio at the surface which is greater than in the bulk of the SAPO. Preferably the SM-3 has a composition in terms of mole ratios of oxides on an anhydrous basis of:

$$mR:Al_2O_3:nP_2O_5:qSiO_2$$

wherein "R" represents at least one organic templating agent present in the intracrystalline pore system, "m" represents the moles of "R" present and has a value such that there are from 0.02 to 2 moles of "R" per mole of alumina, n has a value of from 0.96 to 1.1 and preferably 0.96 to 1, and q has a value of from 0.1 to 4 and preferably 0.1 to 1. Miller '424 is incorporated herein by reference for its teachings with respect to preparation and properties of the preferred SM-3.

The non-zeolitic molecular sieve preferably is composited with a binder for convenient formation of catalyst particles in a proportion of about 5 to 100 mass % NZMS and 0 to 95 mass-% binder, with the NZMS preferably comprising from about 10 to 90 mass-% of the composite. The binder should be porous, adsorptive support having a surface area of about 25 to about 500 m²/g, uniform in composition and relatively refractory to the conditions utilized in the hydrocarbon conversion process. By the term "uniform in composition," it is meant that the support is unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention carrier materials which have traditionally been utilized in hydrocarbon conversion catalysts such as: (1) refractory inorganic oxides such as alumina, titania, zirconia, chromia, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgite clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO—Al_2O_3$ where M is a metal having a valence of 2; and (6) combinations of materials from one or more of these groups.

The preferred refractory inorganic oxide for use in the present invention is alumina. Suitable alumina materials are the crystalline aluminas known as the gamma-, eta-, and theta-alumina, with gamma- or eta-alumina giving best results. A particularly preferred alumina is that which has been characterized in U.S. Pat. Nos. 3,852,190 and 4,012,313 as a by-product from a Ziegler higher alcohol synthesis reaction as described in Ziegler's U.S. Pat. No. 2,892,858. For purposes of simplification, such an alumina will be hereinafter referred to as a "Ziegler alumina". Ziegler alumina is presently available from the Vista Chemical Company under the trademark "Catapal" or from Condea Chemie GmbH under the trademark "Pural." This material is an extremely-high-purity pseudoboehmite which, after calcination at a high temperature, has been shown to yield a high purity gamma-alumina.

An alternative preferred binder is a form of amorphous silica. The preferred amorphous silica is a synthetic, white, amorphous silica (silicon dioxide) powder which is classed as wet-process, hydrated silica. This type of silica is produced by a chemical reaction in a water solution, from which it is precipitated as ultra-fine, spherical particles. It is preferred that the BET surface area of the silica is in the range from about 120 to 160 m²/g. A low content of sulfate salts is desired, preferably less than 0.3 wt. %. It is especially preferred that the amorphous silica binder be nonacidic, e.g., that the pH of a 5% water suspension be neutral or basic (pH about 7 or above).

A preferred shape for the catalyst composite is an extrudate. The well-known extrusion method initially involves mixing of the non-zeolitic molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from 30 to 50 wt. % being preferred. The dough then is extruded through a die pierced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

A favored alternative shape of the composite is a sphere, continuously manufactured by the well-known oil drop method. Preferably, this method involves dropping the mixture of molecular sieve, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50–200° C. and subjected to a calcination procedure at a temperature of about 450–700° C. for a period of about 1 to about 20 hours. This treatment effects conversion of the hydrogel to the corresponding alumina matrix.

A platinum-group metal, including one or more of platinum, palladium, rhodium, ruthenium, osmium, and iridium, is an essential component of the present catalyst. The preferred platinum-group metal is platinum. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state. The platinum-group metal component generally comprises from about 0.01 to about 2 mass-% of the final catalyst composite, calculated on an elemental basis.

The platinum-group metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the sieve component and binder. Yet another method of effecting a suitable metal distribution is by compositing the metal component with the binder prior to co-extruding the sieve and binder. Complexes of platinum-group metals which may be employed according to the above or other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diamminepalladium (II) hydroxide, tetramminepalladium (II) chloride, and the like.

It is within the scope of the present invention that the catalyst composite may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art to effect a homogeneous or stratified distribution.

The catalyst composite of the present invention may contain a halogen component. The halogen component may be either fluorine, chlorine, bromine or iodine or mixtures thereof, with chlorine being preferred. The halogen component is generally present in a combined state with the inorganic-oxide support. The optional halogen component is preferably well dispersed throughout the catalyst and may comprise from more than 0.2 to about 15 wt. %, calculated on an elemental basis, of the final catalyst. The halogen component may be incorporated in the catalyst composite in any suitable manner, either during the preparation of the inorganic-oxide support or before, while or after other catalytic components are incorporated.

The catalyst composite is dried at a temperature of from about 100° to about 320° C. for a period of from about 2 to about 24 or more hours and, usually, calcined at a temperature of from 400° to about 650° C. in an air atmosphere for a period of from about 0.1 to about 10 hours until the metallic compounds present are converted substantially to the oxide form. If desired, the optional halogen component may be adjusted by including a halogen or halogen-containing compound in the air atmosphere.

The resultant calcined composite optimally is subjected to a substantially water-free reduction step to insure a uniform and finely divided dispersion of the optional metallic components. The reduction optionally may be effected in the process equipment of the present invention. Substantially pure and dry hydrogen (i.e., less than 20 vol. ppm $H_2O$) preferably is used as the reducing agent in this step. The reducing agent contacts the catalyst at conditions, including a temperature of from about 200° to about 650° C. and for a period of from about 0.5 to about 10 hours, effective to reduce substantially all of the Group VII metal component to the metallic state. In some cases the resulting reduced catalyst composite may also be beneficially subjected to presulfiding by a method known in the art to incorporate in the catalyst composite from about 0.05 to about 0.5 mass-% sulfur calculated on an elemental basis.

EXAMPLES

The following examples are presented only to illustrate certain specific embodiments of the invention, and should not be construed to limit the scope of the invention as set forth in the claims. There are many possible other variations, as those of ordinary skill in the art will recognize, which are within the spirit of the invention.

Samples of SM-3 silicoaluminophosphate were prepared for testing as isomerization catalysts in the process of the invention. The SM-3 was prepared according to the teachings of U.S. Pat. No. 4,943,424 (Miller) and had characteristics as disclosed in the '424 patent.

Samples of SAPO-11 silicoaluminophosphate not of the invention were prepared in accordance with the teachings of U.S. Pat. No. 4,440,871 and as described hereunder. Molar proportions of 50 moles water to 1.8 moles of orthophosphoric acid as 85 mass-% H₃PO₄ were combined, and 1.0 moles of alumina was added to the solution as Versal 250 with stirring of the mixture. Silica then was added as HiSil 250 in a molar proportion of 0.2 moles. The directing agent was di-n-propylamine, added in a proportion of 1.8 moles. The composition of the reaction mixtures therefore was as follows:

$$1.8(Pr_2NH):0.2SiO_2:Al_2O_3:0.9P_2O_5:50H_2O$$

SAPO-11 seed amounting to 1.0 mass-% of the oxides was added and the reaction mixture was heated gradually to 195° C. and held at that temperature for 12 hours. The solid reaction product was recovered by centrifugation, washed with water and dried in air at 100° C. Certain of the synthesis powders were bound with alumina as described below and then were calcined at 650° C. in flowing air to remove the synthesis template and set the silica binder of the bound catalyst samples. The unbound control SAPO-11, not of the invention, was designated as "Control."

Example I

The advantage of the process of the invention was demonstrated in a series of microreactor tests. Unbound catalysts were loaded in the microreactor in a quantity of 250 mg. Meta-xylene was fed to the reactor in a hydrogen atmosphere at varying temperatures. The test results showed conversion of meta-xylene as follows for the SM-3 silicoaluminophosphate in comparison to the control SAPO-11 not of the invention:

|         | 400° C. | 500° C. |
|---------|---------|---------|
| SM-3    | 39.14   | 47.44   |
| Control | 3.27    | 9.2     |

The SM-3 showed a substantial advantage over the control catalyst in meta-xylene conversion at both temperatures, as well as demonstrating favorable selectivity as described hereinbelow.

Example II

The selectivity of the process of the invention was demonstrated in comparison to the use of a zeolitic catalyst of the art. A spherical control catalyst comprising about 10 mass-% MOR in an alumina matrix and containing about 0.3 mass-% platinum was prepared by oil dropping according to the teachings of U.S. Pat. No. 2,620,314. The control catalyst was loaded in a microreactor in a quantity of 250 mg, and meta-xylene was fed to the reactor in a hydrogen atmosphere at varying temperatures. Conversion of meta-xylene was about 46.8% at 400° C. and 48.7% at 500° C. The para- to ortho-xylene ratio in the product was determined for the control and measured for the SM-3 silicoaluminophosphate tested according to Example I. Results were as follows:

|         | 400° C. | 500° C. |
|---------|---------|---------|
| SM-3    | 1.24    | 1.06    |
| Control | 1.10    | 0.99    |

Example III

The SM-3 silicoaluminophosphate was composited with alumina and tetramine platinic chloride at alternative platinum levels to aid in formulating the optimum catalyst of the invention. The composites comprised about 60 mass-% SM-3 and 40 mass-% alumina. Tetramine platinic chloride was incorporated into the composites to effect platinum contents of 0.28 and 0.14 mass-%, respectively, on an elemental basis, and the catalysts were calcined and reduced.

The catalysts were evaluated using a pilot plant flow reactor processing a non-equilibrium C₈-aromatic feed having the following composition in mass-%:

| ethylbenzene | 17% |
|---|---|
| meta-xylene | 58% |
| ortho-xylene | 25% |

This feed was contacted with 100 cc of catalyst at a liquid hourly space velocity of 2, and a hydrogen/hydrocarbon mole ratio of 4. Reactor temperature was adjusted to effect a favorable conversion level. Conversion is expressed as the disappearance per pass of ethylbenzene. C₈-aromatic loss is primarily to benzene and toluene, with smaller amounts of light gases being produced. Results were as follows:

| Catalyst mass-% Pt | 0.28 | 0.14 |
|---|---|---|
| Temperature, °C. | 386 | 380 |
| Ethylbenzene conversion, % | 28 | 24.5 |
| C₈-aromatics loss, % | 2.8 | 2.8 |

Example IV

Catalyst samples were prepared and tested to illustrate the effect of platinum location on the performance of the catalyst. Catalyst A was prepared as in Example III by coextruding SM-3 silicoaluminophosphate and alumina in a 60/40 mass ratio with tetramine platinic chloride, calcining and reducing to effect a catalyst containing 0.28 mass-% platinum. Catalyst B was prepared by first compositing alumina and tetramine platinic chloride, followed by coextruding with SM-3, calcining and reducing to effect a catalyst having the same overall composition as Catalyst A.

The catalysts were evaluated using a pilot plant flow reactor processing the same non-equilibrium C₈-aromatic feed as in Example III. This feed was contacted with 100 cc of catalyst at a liquid hourly space velocity of 2 hr⁻¹ and a hydrogen/hydrocarbon mole ratio of 4. Reactor temperature was adjusted to effect a favorable conversion level. Conversion is expressed as the disappearance per pass of ethylbenzene, and C₈-aromatic loss is primarily to benzene and toluene. Results were as follows:

| Catalyst: | A | B |
|---|---|---|
| Temperature, °C. | 386 | 386 |
| Ethylbenzene conversion, % | 28 | 27.5 |
| C₈-aromatics loss, % | 2.8 | 2.7 |

We claim:

1. A process for the isomerization of a feed mixture of xylenes and ethylbenzene comprising contacting the feed mixture in the presence of hydrogen in an isomerization zone with a catalyst composite comprising from about 0.1 to 2 mass-% of a platinum component, from about 10 to 90 mass-% of an SM-3 crystalline silicoaluminophosphate molecular sieve, having a P₂O₅-to-alumina mole ratio at the surface of the silicoaluminophosphate (SAPO) of about 0.80 or less, a $P_2O_5$-to-alumina mole ratio in the bulk of the SAPO of 0.96 or greater, and a silica-to-alumina ratio at the surface which is greater than in the bulk of the SAPO, and an inorganic-oxide binder at isomerization conditions comprising a temperature of from about 300° to 500° C., a pressure of from about 1 to 50 atmospheres, a liquid hourly space velocity of from about 0.5 to 10 $hr^{-1}$ and a hydrogen-to-hydrocarbon mole ratio of from about 0:5:1 to 25:1 to obtain an isomerized product comprising a higher proportion of para-xylene than in the feed mixture with a $C_8$-aromatics loss relative to the feed mixture of less than about 4 mass-%.

2. The process of claim 1 wherein the inorganic-oxide binder comprises one or both of alumina and silica.

3. The process of claim 1 wherein the inorganic-oxide binder comprises alumina.

4. The process of claim 1 wherein ortho-xylene is recovered from one or both of the isomerized product and fresh $C_8$-aromatic feed.

5. The process of claim 1 further comprising recovery of para-xylene by selective adsorption from the isomerized product and a fresh $C_8$-aromatics feed.

* * * * *